(12) United States Patent
Okazoe et al.

(10) Patent No.: US 7,071,272 B2
(45) Date of Patent: Jul. 4, 2006

(54) METHOD FOR PREPARING UNSATURATED COMPOUND BY PYROLYSIS REACTION

(75) Inventors: Takashi Okazoe, Yokohama (JP); Kunio Watanabe, Yokohama (JP); Shin Tatematsu, Yokohama (JP); Masakuni Sato, Yokohama (JP); Hidenobu Murofushi, Yokohama (JP); Koichi Yanase, Ichihara (JP); Yasuhiro Suzuki, Ichihara (JP)

(73) Assignee: Asahi Glass Company, Limited, Tokyo (JP)

( * ) Notice: Subject to any disclaimer, the term of this patent is extended or adjusted under 35 U.S.C. 154(b) by 152 days.

(21) Appl. No.: 10/307,388

(22) Filed: Dec. 2, 2002

(65) Prior Publication Data

US 2003/0139570 A1 Jul. 24, 2003

Related U.S. Application Data

(63) Continuation of application No. PCT/JP01/01735, filed on Mar. 6, 2001.

(30) Foreign Application Priority Data

Jun. 2, 2000 (JP) ............................. 2000-166773

(51) Int. Cl.
*C08F 16/24* (2006.01)

(52) U.S. Cl. ................. 526/247; 526/242; 526/252; 526/253; 562/852; 205/430

(58) Field of Classification Search ............... 526/252, 526/242, 247, 253; 562/852; 205/430
See application file for complete search history.

(56) References Cited

U.S. PATENT DOCUMENTS

| | | | | |
|---|---|---|---|---|
| 3,114,778 A | | 12/1963 | Fritz | 568/674 |
| 3,282,875 A | | 11/1966 | Connolly | 524/795 |
| 3,321,532 A | | 5/1967 | Lorenz | 260/614 |
| 3,450,684 A | | 6/1969 | Darby | 526/247 |
| 3,641,104 A | * | 2/1972 | Anderson et al. | 558/449 |
| 3,674,758 A | | 7/1972 | Carlson | 525/326.2 |
| 4,138,426 A | | 2/1979 | England | 558/449 |
| 4,358,412 A | * | 11/1982 | Ezzell et al. | 558/142 |
| 4,804,727 A | * | 2/1989 | Ezzell et al. | 526/247 |
| 4,834,922 A | | 5/1989 | Ezzell et al. | 558/449 |
| 5,449,438 A | * | 9/1995 | Jagau et al. | 201/10 |
| 5,466,877 A | * | 11/1995 | Moore | 562/852 |
| 6,187,948 B1 | * | 2/2001 | Negishi et al. | 560/227 |
| 2003/0139570 A1 | | 7/2003 | Okazoe et al. | |

FOREIGN PATENT DOCUMENTS

| | | |
|---|---|---|
| EP | 1 352 892 | 10/2003 |
| GB | 1 424 170 | 4/1974 |
| JP | 39-21228 | 9/1939 |
| JP | 52-89603 | 7/1977 |
| JP | 2-311438 | 12/1990 |
| JP | 6-340719 | 12/1994 |
| RU | 2 056 437 | 3/1996 |
| RU | 2 128 667 | 4/1999 |
| RU | 2 144 043 | 1/2000 |
| SU | 178104 | 2/1966 |
| SU | 207139 | 2/1968 |
| SU | 379556 | 8/1973 |
| SU | 400110 | 4/1974 |
| WO | WO 90/03353 | 4/1990 |
| WO | WO 00/56694 | 9/2000 |
| WO | WO 01/16085 A1 | 3/2001 |
| WO | WO 02/10107 | 2/2002 |
| WO | WO 02/26686 | 4/2002 |
| WO | WO 02/26687 | 4/2002 |
| WO | WO 02/26688 | 4/2002 |
| WO | WO 02/26689 | 4/2002 |
| WO | WO 02/40437 | 5/2002 |
| WO | WO 02/44138 | 6/2002 |
| WO | WO 02/055471 | 7/2002 |

OTHER PUBLICATIONS

Polyfluorinated Alkyl Vinyl Ethers, II, Synthesis of Perfluorinated Cyclohexylmethyl Vinyl Ether, 1995.
Okazoe, Takashi, et al., "Synthesis of Versatile Poly– and Perfluorinated Compound by Utilizing Direct Fluorination, A New Route to Perfluoro(Propyl Vinyl Ether) Monomer: Synthesis of Perfluoro(2–propoxypropionyl) Fluoride from Non–Fluorinated Compounds" Advanced Synthesis & Catalysis, 343, No. 2, pp. 215–219, 2001.
Yuminov, V.S., et al., "Polyfluorinated alkyl vinyl ethers. II. Synthesis of perfluorinated cyclohexylmethyl vinyl ether," Zh. Org. Khim., (1995), vol. 31, No. 8, pp. 1145–1148.
U.S. Appl. No. 10/891,155, filed Jul. 15, 2004, Okazoe et al.
U.S. Appl. No. 10/307,388, filed Dec. 2, 2002, Okazoe et al.
U.S. Appl. No. 10/352,166, filed Jan. 28, 2003, Okazoe et al.
U.S. Appl. No. 10/340,634, filed Jan. 13, 2002, Okazoe et al.
U.S. Appl. No. 10/372,765, filed Feb. 26, 2003, Okazoe et al.
U.S. Appl. No. 10/307,388, filed Dec. 2, 2002, Watanabe et al.
U.S. Appl. No. 10/397,423, filed Mar. 27, 2003, Watanabe et al.
U.S. Appl. No. 10/397,230, filed Mar. 27, 2003, Okazoe et al.
U.S. Appl. No. 10/397,521, filed Mar. 27, 2003, Okazoe et al.
U.S. Appl. No. 10/442,227, filed May 21, 2003, Ito et al.
U.S. Appl. No. 10/421,924, filed Apr. 24, 2003, Okazoe et al.
U.S. Appl. No. 10/833,048, filed Apr. 28, 2004, Okazoe et al.
U.S. Appl. No. 10/619,784, filed Jul. 16, 2003, Okazoe et al.
U.S. Appl. No. 10/915,423, filed Aug. 11, 2004, Okazoe et al.

* cited by examiner

*Primary Examiner*—David W. Wu
*Assistant Examiner*—Henry S. Hu
(74) *Attorney, Agent, or Firm*—Oblon, Spivak, McClelland, Maier & Neustadt, P.C.

(57) ABSTRACT

The present invention provides a method for preparing a compound of $CF_3CF_2CF_2OCF=CF_2$ by pyrolyzing a compound expressed by $CF_3CF_2CF_2OCF(CF_3)COOCF_2CF(CF_3)OCF_2CF_2CF_3$ in a gas phase at a temperature of from 200° C. to 500° C.

14 Claims, No Drawings

METHOD FOR PREPARING UNSATURATED COMPOUND BY PYROLYSIS REACTION

TECHNICAL FIELD

The present invention relates to a method for preparing an unsaturated compound usable as a useful resin starting material and a method for preparing a polymer by using the unsaturated compound.

BACKGROUND ART

An unsaturated compound such as perfluoro(alkyl alkenyl ether) is useful as a starting material monomer for a fluororesin. A fluororesin has excellent properties in respect of heat resistance and chemical resistance, and it is therefore widely used. Heretofore, perfluoro(alkyl alkenyl ether) is industrially prepared by dimerization reaction of perfluoroepoxides or by reacting perfluoroalkanoic acid fluoride with perfluoroepoxides in the presence of an alkali metal fluoride to form perfluoro(2-alkoxyalkanoic acid)fluorides, followed by heating reaction in the presence of glass beads or an alkali metal salt such as soda ash (Methods of Organic Chemistry, 4, Vol. 10b, Part 1, p. 703, etc.)

Also, a reaction of obtaining an acid fluoride compound by heating a perfluorinated alkyl ester compound having a carbon number of at least 16 is known as a reaction of pyrolyzing an ester bond (J. Am. Chem. Soc., 120, 7117 (1998)).

DISCLOSURE OF THE INVENTION

A conventional method for preparing a perfluoro(alkyl alkenyl ether) raised an economically unfavorable problem as an industrial preparation method since its reaction was hardly controlled and the price of a starting material was high.

BEST MODE FOR CARRYING OUT THE INVENTION

An object of the present invention is to provide a method for preparing an unsaturated compound in one step by using a cheaply available compound as a starting material.

That is, the present invention provides a method for preparing a compound expressed by the following formula 2 by pyrolyzing a compound having at least one partial structure expressed by the following formula 1,

wherein each of $R^b$, $R^c$, $R^d$ and $R^e$ is independently a hydrogen atom, a halogen atom or a monovalent organic group unchangeable by pyrolysis reaction, and two members selected from the group consisting of $R^b$, $R^c$, $R^d$ and $R^e$ may be connected with each other to form a divalent organic group unchangeable by pyrolysis, and the remaining two members may be connected with each other to form a divalent organic group unchangeable by pyrolysis, or each of the remaining two members may be independently a hydrogen atom, a halogen atom or a monovalent organic group unchangeable by pyrolysis reaction, and X is a halogen atom.

In the present specification, a compound expressed by the formula 1A is described as "Compound (1A)". Compounds expressed by other formulae are described also in the same manner as above.

In the present specification, an organic group means a group having a carbon atom as an essential component, and may be any one of saturated or unsaturated structures. The organic group is preferably a hydrocarbon group, a hetero atom-containing hydrocarbon group, a halogenohydrocarbon group or a halogeno(hetero atom-containing hydrocarbon) group.

The hydrocarbon group may be any one of an aliphatic hydrocarbon group or an aromatic hydrocarbon group, and is preferably an aliphatic hydrocarbon group. The aliphatic hydrocarbon group may contain a single bond, a double bond or a triple bond as a carbon-carbon bond. The aliphatic hydrocarbon group may be any one of a linear chain structure, a branched chain structure, a cyclic chain structure or a structure partially having a cyclic chain structure.

The hydrocarbon group is preferably a saturated hydrocarbon group. Examples of a monovalent saturated hydrocarbon group include preferably an alkyl group, a cycloalkyl group or a monovalent saturated hydrocarbon group having a cycloalkyl part (such as a cycloalkylalkyl group). Examples of the alkyl group include preferably a $C_1$–$C_{10}$ alkyl group, particularly a methyl group, an ethyl group or a propyl group. Examples of the cycloalkyl group include a $C_3$–$C_6$ cyclic cycloalkyl group, preferably at least one hydrogen atom of which is substituted with an alkyl group. Examples of the cycloalkylalkyl group include preferably a group having one hydrogen atom of a $C_1$–$C_3$ alkyl group substituted with the above cycloalkyl group, such as a cyclohexylmethyl group.

Examples of a divalent saturated hydrocarbon group include an alkylene group, a group having a cycloalkylene part, a divalent saturated hydrocarbon group having a cycloalkyl part (such as a cycloalkylalkylene group), and the like.

Examples of a halogen atom include a fluorine atom, a chlorine atom, a bromine atom or an iodine atom, and a fluorine atom, a chlorine atom or a bromine atom is preferable, and particularly a fluorine atom or a chlorine atom is preferable.

A halogenohydrocarbon group means a group having at least one hydrogen atom of the hydrocarbon group substituted with a halogen atom. The halogenohydrocarbon group may contain a hydrogen atom or may not contain a hydrogen atom. The halogen atom in the halogenohydrocarbon group is preferably a fluorine atom or a chlorine atom. Also, a group having a part of hydrogen atoms present in the hydrocarbon group substituted with a halogen atom is called as a partially halogenated hydrocarbon group. The partially halogenated hydrocarbon group contains a hydrogen atom. Also, a perhalogeno-hydrocarbon group means a compound having all of hydrogen atoms present in the group substituted with a halogen atom. The perhalogeno-hydrocarbon group does not contain a hydrogen atom. The halogen atoms present in the halogeno group and the perhalogeno group may be one kind or two or more kinds.

A halogeno-monovalent saturated hydrocarbon group may have a linear chain structure, a branched chain structure or a partially cyclic structure, and examples of the halogenomonovalent saturated hydrocarbon group include a fluoroalkyl group or a fluoro(partially chlorinated alkyl) group. The halogeno-monovalent hydrocarbon group has preferably a carbon number of from 1 to 20. Examples of the perhalogeno-monovalent saturated hydrocarbon group include preferably a perfluoroalkyl group or a perfluoro (partially chlorinated alkyl) group (i.e. a group in which all of hydrogen atoms in the partially chlorinated alkyl group are substituted with fluorine atoms). The halogenomonovalent hydrocarbon group has preferably a carbon number of from 1 to 20. Examples of this group are illustrated below.

A halogeno-divalent saturated hydrocarbon group may have a linear chain structure, a branched chain structure or a partially cyclic structure, preferable examples of which include a fluoroalkylene group or a fluoro(partial chloroalkylene) group. Examples of a perhalogeno-divalent saturated hydrocarbon group include preferably a perfluoroalkylene group or a perfluoro(partial chloroalkylene) group (i.e. a group having all of hydrogen atoms in the partial chloroalkylene group substituted with fluorine atoms).

A hetero atom-containing hydrocarbon group means a group comprising a carbon atom, a hydrogen atom and a hetero atom such as an oxygen atom, a nitrogen atom or a sulfur atom. The hetero atom may be a hetero atom itself or a hetero atom group having a hetero atom bonded thereto. The hetero atom and the hetero atom group are preferably not changed by pyrolysis reaction, and an ether type oxygen atom (—O—) is particularly preferable as the hetero atom. The hetero atom-containing hydrocarbon group preferably has a carbon number of from 1 to 20. The hetero atom-containing hydrocarbon group is preferably a group having a divalent hetero atom or a divalent hetero atom group inserted between carbon-carbon atoms of the hydrocarbon group, a group having a hetero atom bonded to a carbon atom in the hydrocarbon group, or a group having a divalent hetero atom or a divalent hetero atom group bonded to a carbon atom of the terminal bond of the hydrocarbon group. An ether type oxygen atom-containing group is particularly preferable as the hetero atom-containing group in respect of utility of a compound, and more particularly a group having an ether type oxygen atom at the bond terminal is preferable.

An ether type oxygen atom-containing alkyl group is preferable as a hetero atom-containing monovalent hydrocarbon group since it is easily available and easily producible and its product has a good utility, and its particularly preferable examples include an alkoxyalkyl group or an alkoxy group. A hetero atom-containing divalent hydrocarbon group is a group having one hydrogen atom working as a bonding link in a hetero atom-containing monovalent hydrocarbon group, and an ether type oxygen atom-containing alkylene group is preferable.

A halogeno(hetero atom-containing hydrocarbon) group is preferably a fluoro(hetero atom-containing hydrocarbon) group or a fluoro(partially chlorinated(hetero atom-containing hydrocarbon)) group. The halogeno(hetero atom-containing hydrocarbon) group has preferably a carbon number of from 1 to 20. A perhalogeno(hetero atom-containing hydrocarbon) group is preferably a perfluoro (hetero atom-containing hydrocarbon) group or a perfluoro (partial chloro(hetero atom-containing hydrocarbon)) group.

A halogeno(hetero atom-containing monovalent hydrocarbon) group may have a linear chain structure or a branched chain structure. The halogeno(hetero atom-containing monovalent saturated hydrocarbon) group is preferably a fluoro(hetero atom-containing alkyl) group or a fluoro(partially chloro(hetero atom-containing alkyl)) group. A perhalogeno(hetero atom-containing monovalent saturated hydrocarbon) group is preferably a perfluoro (alkoxyl) group or a perfluoro(partially chloro(alkoxyl)) group.

A halogeno(hetero atom-containing divalent saturated hydrocarbon) group is a group having one hydrogen atom working as a bonding link in a halogeno(hetero atom group-containing monovalent saturated hydrocarbon) group, and its preferable examples include a fluoro(ether type oxygen atom-containing divalent alkylene) group or a fluoro (partially chlorinated(ether type oxygen atom-containing divalent alkylene)) group. A perhalogeno(hetero atom-containing divalent saturated hydrocarbon) group is preferably a perfluoro(ether type oxygen atom-containing divalent alkylene) group or a perfluoro(partially chloro(ether type oxygen atom-containing divalent alkylene)) group.

In the present invention, a compound having at least one partial structure expressed by the Formula 1 (hereinafter referred to as "Compound (I)") is pyrolyzed.

When each of $R^b$ to $R^e$ of Compound (I) is an organic group unchangeable by pyrolysis, the organic group is an organic group having a chemical structure unchangeable before and after the pyrolysis reaction in the present invention. Examples of the organic group include a group having no partial structure of "COOCF$_2$C—CX$^a$ (wherein X$^a$ is a halogen atom)" in the group (hereinafter referred to as "group (A)") or a group having no chemically unstable structure under the reaction conditions of pyrolysis.

Examples of $R^b$ to $R^e$ of which are the organic groups unchangeable by pyrolysis include a hydrocarbon group or a halogenohydrocarbon group. A hetero atom-containing hydrocarbon group or a halogeno(hetero atom-containing hydrocarbon) group is usually a group unchangeable by pyrolysis, except for such a case that a hetero atom or a hetero atom group in the group is changed by pyrolysis reaction (such as a group (A)). The above explanation concerning an organic group having a chemical structure unchangeable before and after pyrolysis reaction is applicable also to both monovalent and divalent organic groups, and a group (A) is removed from the following explanation concerning $R^b$ to $R^e$.

$R^b$ to $R^e$ are preferably a saturated hydrocarbon group, a halogeno saturated hydrocarbon group, a hetero atom-containing saturated hydrocarbon group or a halogeno hetero atom-containing saturated hydrocarbon group. Further, $R^b$ to $R^e$ are preferably these groups containing a fluorine atom, preferable examples of which include a perfluoro saturated hydrocarbon group, a perfluoro(ether type oxygen atom-containing saturated hydrocarbon) group, a perfluoro (partially chlorinated saturated hydrocarbon) group or a perfluoro(partially chlorinated(ether type oxygen atom-containing hydrocarbon)) group (hereinafter, these groups are referred to as "group ($R^F$)").

When the group ($R^F$) is a monovalent group, its carbon number is from 1 to 20. Preferable examples of this group include a perfluoroalkyl group, a perfluoro(ether type oxygen atom-containing alkyl) group, a perfluoro(partially chlorinated alkyl) group or a perfluoro(partially chlorinated (ether type oxygen atom-containing alkyl)) group (hereinafter, these groups are referred to as "group ($R^{F1}$)").

When the group ($R^F$) is a divalent group, its carbon number is preferably from 1 to 20. Examples of this group include a perfluoroalkylene group, a perfluoro(ether type oxygen atom-containing alkylene) group, a perfluoro (partially chlorinated alkylene) group or a perfluoro (partially chlorinated(ether type oxygen atom-containing alkylene)) group (hereinafter, these groups are referred to as "group ($R^{F2}$)").

Examples of these groups ($R^F$) are concretely illustrated in compounds concretely described below. In the present invention, Compound (I) is pyrolyzed. Compounds (I) may contain at least two partial structures of the Formula 1, and in such a case, Compound (2) corresponding to said partial structure is formed. Usually, it is preferable that the partial structure of the Formula 1 is one. Further, Compound (IA) is preferable as Compound (I).

$$R^a COOCF_2 CR^b R^c\text{—}CXR^d R^e \qquad \text{Formula 1A}$$

$R^a$ is a hydrogen atom, a halogen atom or a monovalent organic group. However, $R^b$, $R^c$, $R^d$, $R^e$ and X are as defined above. X is preferably a fluorine atom, but a chlorine atom is preferable in respect that it is easily susceptible to pyrolysis reaction.

When $R^a$ is a monovalent organic group, $R^a$ is preferably $R^1 CF(CF_3)$—, $R^2 OCF(CF_3)$—, $R^3 CF_2 CF_2$— or $R^4 OCF_2 CF_2$— (wherein each of $R^1$ to $R^4$ is independently a monovalent organic group, and is preferably a monovalent group ($R^F$), particularly a group ($R^{F1}$)). When $R^a$ is these groups, Compound (3) expressed by $R^a COF$ (Formula 3) formed by pyrolysis reaction is chemically converted to $R^1 CF=CF_2$, $R^2 OCF=CF_2$, $R^3 CF=CF_2$ or $R^4 OCF=CF_2$ under conditions of pyrolysis reaction. These compounds having a —CF=CF_2 structure are useful compounds having a polymerizable unsaturated bond. $R^a$ is preferably a group expressed by $CXR^d R_e\text{—}CR^b R_c\text{—}$ (wherein $R^b$ to $R^e$ are as defined above, and X is a halogen atom), and particularly preferable examples of this group include $R_1 CF(CF_3)$—, $R^2 OCF(CF_3)$—, $R^3 CF_2 CF_2$— or $R^4 OCF_2 CF_2$—.

Further, the reaction of the present invention is a particularly useful method as a method for forming a fluorine-containing unsaturated compound. Compound ($1A^F$) is preferable as Compound (I), and Compound (1B) is particularly preferable.

$$R^{af} COOCF_2 CR^{bf} R^{cf}\text{—}CXR^{df} R^{ef} \qquad \text{Formula 1}A^F$$

In the above formula, $R^{af}$ is a fluorine atom or a perfluoro-monovalent organic group, each of $R^{bf}$, $R^{cf}$, $R^{df}$ and $R^{ef}$ is independently a fluorine atom or a fluorine-containing monovalent organic group unchangeable by pyrolysis reaction, or two members selected from the group consisting of $R^{bf}$, $R^{cf}$, $R^{df}$ and $R^{ef}$ may be connected with each other to form a fluorine-containing divalent organic group unchangeable by pyrolysis reaction, and the remaining two members may be connected with each other to form a fluorine-containing divalent organic group unchangeable by pyrolysis reaction, or each of the remaining two members may be independently a fluorine atom or a fluorine-containing monovalent organic group unchangeable by pyrolysis reaction, and the number of the fluorine-containing divalent organic group may be one or two, but preferably one, and X is a halogen atom.

Particularly, a compound of the following Formula 1B wherein $R^a$ is $CXR^d R^e\text{—}CR^b R^c$—, is preferable as a product by pyrolysis reaction since Compound (2) becomes a main product. In this case, $FCO\text{—}CR^b R^c\text{—}CXR^d R^e$ (Formula 3B) formable in the process of the reaction is converted to Compound (2) under the conditions of pyrolysis reaction. When substantially all of Compound (3B) are converted to Compound (2), separation and purification steps can be omitted since substantially Compound (2) only is formed as a product.

$$CXR^d R^e\text{—}CR^b R^c\text{—}COOCF_2 CR^b R^c\text{—}CXR^d R^e \qquad \text{Formula 1B}$$

In the above formula, $R^b$, $R^c$, $R^d$, $R^e$ and X are as defined above.

Further, Compound ($1B^F$) is preferable as Compound (1B) in respect of utility of a product.

$$CXR^{df} R^{ef}\text{—}CR^{bf} R^{cf}\text{—}COOCF_2 CR^{bf} R^{cf}\text{—}CXR^{df} R^{ef} \qquad \text{Formula 1}B^F$$

In the above formula, $R^{bf}$, $R^{cf}$, $R^{df}$, $R^{ef}$ and X are as defined above.

In Compound (1A) and Compound (1B), at least one group selected from $R^b$, $R^c$, $R^d$ and $R^e$ is preferably a group having an ether type oxygen atom at the terminal (such as a perfluoro(alkoxyl group) or a perfluoro(partially chlorinated (alkoxyl)) group) and the remaining group (if any) is preferably a fluorine atom, in respect of utility of Compound (2) form. Particularly, it is preferable that any one of $R^b$, $R^c$, $R^d$ and $R^e$ groups is a perfluoro(alkoxyl) or perfluoro(partially chlorinated(alkoxyl)) group and the remaining three groups are fluorine atoms. Also, when $R^b$, $R^c$, $R^d$ and $R^e$ form a divalent organic group, it is preferable that the divalent organic group has an ether type oxygen atom at the both bonding terminals.

Also, when $R^a$ in Compound (1A) is selected so as to make a large boiling point difference between Compound (2) and Compound (3) formed by pyrolysis reaction, it is preferable since the Compound (2) and the Compound (3) are easily separable. For example, this is such a case wherein $R^a$ is a fluorine atom or $R^a$ has a large molecular weight. The boiling point difference is preferably at least 2° C., more preferably at least 20° C. Further, by making the molecular weight of $R^a$ large, it is preferable to make the boiling point of Compound (3) at least 2° C., particularly at least 20° C., higher than that of Compound (2).

Examples of Compound (1A) are illustrated below. In the following examples, $Cy^F$ is a perfluoro(cyclohexyl) group.

$CF_3 CF_2 CF_2 OCF(CF_3) COOCF_2 CF(CF_3) OCF_2 CF_2 CF_3$,
$CF_3 CF_2 COOCF_2 CF(CF_3) OCF_2 CF_2 CF_3$,
$CF_2 ClCFClCF_2 CF_2 O(CF_3) CFCOOCF_2 CF(CF_3) OCF_2 CF_2 CFClCF_2 C_1$,
$CF_2 ClCFClCF_2 CF(CF_3) OCF(CF_3) COOCF_2 CF(CF_3) OCF(CF_3) CF_2 CFClCF_2 Cl$,
$CF_3 CF_2 CF_2 OCF(CF_3) COOCF_2 CF(CF_3) OCF_2 CF_2 CFClCF_2 Cl$,
$CF_3 CF_2 CF_2 OCF(CF_3) COOCF_2 CF(CF_3) OCF_2 Cy^F$,
$CF_3 CF_2 CF_2 OCF(CF_3) COOCF_2 CF(CF_3) O(CF_2)_9 CF_3$,

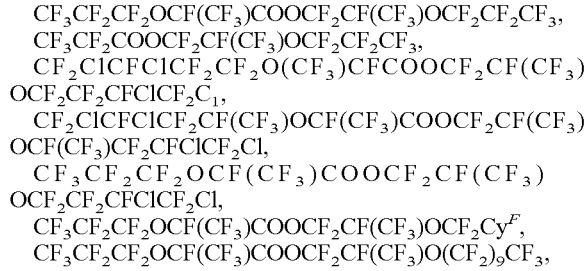

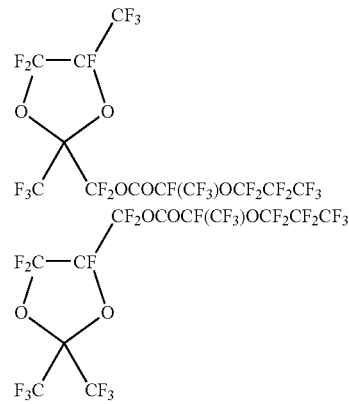

In the present invention, Compound (2) is obtained by the pyrolysis reaction of Compound (I). The pyrolysis reaction is carried out by heating. The reaction is usually carried out by gas phase reaction or liquid phase reaction, and the gas phase reaction is preferable since it can be efficiently carried out. It is preferable to select a method and a reaction temperature for the pyrolysis reaction by taking a boiling point and a stability of Compound (I) into consideration.

Further, since the pyrolysis reaction of Compound (I) can be carried out by gas phase reaction, it is preferable to employ a boiling point of at most 350° C. under normal pressure. Also, it is preferable that Compound (I) has a boiling point of at least 50° C. It is preferable to carry out the gas phase reaction by a continuous type reaction. It is preferable to carry out the continuous type reaction by passing a vaporized compound (I) through a heated reaction tube to obtain a formed Compound (2) as an outlet gas and condensing the formed compound to continuously recover.

The reaction temperature for carrying out pyrolysis by gas phase reaction may be optionally varied depending on a structure of Compound (I), but is generally preferably at least 150° C., more preferably from 200° C. to 500° C., most preferably from 250° C. to 450° C. If the reaction temperature is too high, decomposition reaction of the product is caused, thereby lowering a yield. On the contrary, if the reaction temperature is too low, it is not preferable since an amount of $FCOCR^bR^c$—$CXR^dR^e$ formed is increased.

Further, in the present invention, when the pyrolysis reaction is carried out by gas phase reaction, it is preferable to employ a tubular reactor. When using the tubular reactor, a retention time is preferably from 0.1 second to 10 minutes on the basis of a vacant column standard. The reaction pressure is not specially limited. Also, when Compound (I) is a high boiling point compound, it is preferable to carry out the reaction under a reduced pressure. On the contrary, when Compound (I) is a low boiling point compound, it is preferable to carry out the reaction under a pressurized condition so that decomposition of a product can be prevented and a reaction rate is raised.

When carrying out the gas phase reaction by using a tubular reactor, it is preferable to fill glass, an alkali metal salt or an alkali earth metal salt into the reaction tube since it accelerates the reaction. Preferable examples of the alkali metal salt or the alkali earth metal salt include a carbonate or a fluoride. Examples of the glass include a general soda glass, and bead-like glass beads having a raised fluidity are particularly preferable. Examples of the alkali metal salt include sodium carbonate, sodium fluoride, potassium carbonate or lithium carbonate. Examples of the alkali metal as a carbonate include calcium carbonate, calcium fluoride or magnesium carbonate. Also, when a filler material such as glass, an alkali metal salt or an alkali earth metal salt is filled in the reaction tube, it is preferable to use glass beads or light ash of sodium carbonate having a particle size of from 100 to 250 um since they can form a fluidized bed type reaction system.

It is preferable to previously subject these filler materials to dehydrating treatment. It is preferable to carry out the dehydrating treatment by flowing an inert gas such as nitrogen gas at a reaction temperature of gas phase reaction. By carrying out the dehydrating treatment, a yield of pyrolysis reaction can be remarkably improved.

In the gas phase reaction, it is preferable to carry out the reaction in the presence of an inert gas which does not participate directly in the pyrolysis reaction, in order to accelerate vaporization of Compound (I). Examples of the inert gas include nitrogen, carbon dioxide, helium or argon. An amount of the inert gas is preferably from 0.01 to 50 vol % to the amount of Compound (I). If the amount of the inert gas is too large, an amount of recovery of a product is unpreferably lowered. On the other hand, when Compound (I) has a high boiling point, the pyrolysis may be carried out by liquid phase reaction.

In the pyrolysis reaction of Compound (1A), when $R^a$ is a group unchangeable by the pyrolysis reaction or when Compound (3) is not chemically converted, Compound (2) and Compound (3) are formed. On the other hand, when $R^a$ is a group changeable by the pyrolysis reaction and when Compound (3) is chemically converted, Compound (2) becomes a main product. It is preferable that the product of the pyrolysis reaction of the present invention is Compound (2) only or both of Compound (2) and Compound (3). $R^a$, $R^b$, $R^c$, $R^d$ and $R^e$ in Compound (2) and Compound (3) correspond to groups in Compound (1A) used.

Compound (2) is preferably Compound ($2^F$) formed in the pyrolysis reaction of Compound ($1A^F$).

$$CR^{bf}R^{cf}=CR^{df}R^{ef} \qquad \text{Formula } 2^F$$

Further, in view of polymerizability of Compound (2) to be polymerized for producing a polymer, it is preferable that at least one group selected from $R^b$, $R^c$, $R^d$ and $R^e$ is a group having an ether type oxygen atom at the bonding terminal (such as a perfluoro(alkoxyl group) or a perfluoro(partially chlorinated(alkoxyl)) group), and that the remaining groups, if present, are a fluorine atom. Particularly, it is preferable that one group selected from $R^b$, $R^c$, $R^d$ and $R^e$ is a perfluoro(alkoxyl group) or a perfluoro(partially chlorinated)alkoxyl)) group, and that the remaining three groups are fluorine atoms. Also, when $R^b$, $R^c$, $R^d$ and $R^e$ form a divalent organic group, it is preferable that both bonding terminals of the divalent organic group are ether type oxygen atoms.

Examples of Compound (2) are illustrated below. Among the following compounds, Compound (2A) and Compound (2B) are novel compounds useful as a monomer for producing a fluororesin.

$CF_2=CFOCF_2CF_2CF_3$, $CF_2=CFOCF_2CF_2CFClCF_2Cl$, $CF_2=CFOCF_2Cy^F$      2A $CF_2=CFO(CF_2)_9CF_3$      2B

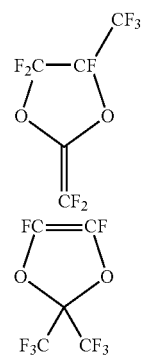

Also, examples of Compound (3) are illustrated below.
$(CF_3)_3CCF_2COF$,
$CF_3CF_2CF_2OCF(CF_3)COF$,
$CF_3CF_2COF$,
$CF_3(CF_2ClCFClCF_2CF_2O)CFCOF$,
$CF_2ClCFClCF_2CF(CF_3)OCF(CF_3)COF$,
$CF_3CF_2CF_2OCF(CF_3)COF$.

Except for the case wherein the product by the pyrolysis is substantially Compound (2) only, it is preferable to separate and purify the product of the pyrolysis reaction by a usual method. Examples of the separation-purification method include distillation method, silica gel column chromatography and the like. Compound (2) and Compound (3)

have a molecular weight lower than those of starting material compounds of pyrolysis reaction, and since they are compounds generally having a lower boiling point, unreacted starting material compounds can be efficiently removed by distillation method.

A method for obtaining Compound (I) of the present invention is not specially limited, and a commercially available compound and a compound obtained by a well-known production method can be used. Particularly, it is preferable to produce Compound ($1A^F$) by liquid-phase fluorination of Compound (5) obtainable by reacting Compound ($3^H$) and Compound (4). A method for producing Compound ($1A^F$) by liquid-phase fluorination reaction in liquid phase is preferable in respect that a starting material (Compound ($3^H$)) is cheap and compounds of various structures are obtainable.

  Formula $3^H$

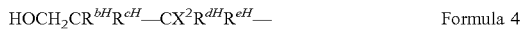  Formula 4

  Formula 5

In the above formulae, $R^{a1}$ is a group equivalent to $R^{af}$ or a group which becomes $R^{af}$ by fluorinating in liquid phase. $R^{bH}$ is a group which becomes $R^{bf}$, $R^{cH}$ is a group which becomes $R^{cf}$, $R^{dH}$ is a group which becomes $R^{df}$ and $R^{eH}$ is a group which becomes $R^{ef}$, respectively and independently by fluorinating in liquid phase.

$X^1$ is respectively and independently a hydrogen atom or a halogen atom, and a fluorine atom is preferable in respect of easiness in the following described continuous production method.

$X^2$ is an atom corresponding to X, and when X is a fluorine atom, it is a hydrogen atom or a fluorine atom, and when X is a halogen atom other than a fluorine atom, it is a halogen atom which is the same as said halogen atom.

When $R^{a1}$ is a group to be fluorinated, it is preferably a group selected from an alkyl group, an ether type oxygen atom-containing alkyl group, a partial chloroalkyl group and a partially chlorinated(ether type oxygen atom-containing alkyl) group, a group having at least one hydrogen atom substituted with a fluorine atom, a group having at least one carbon-carbon single bond substituted with a carbon-carbon double bond or a carbon-carbon triple bond (hereinafter, these groups are referred generally to "($R^{H1}$) group"), or a hydrogen atom.

It is preferable that each of $R^{bH}$, $R^{cH}$, $R^{dH}$ and $R^{eH}$ is independently a ($R^{H1}$) group, a hydrogen atom, or a fluorine atom. Also, it is preferable that two of $R^{bH}$, $R^{cH}$, $R^{dH}$ and $R^{eH}$ are connected with each other to form an alkylene group, an ether type oxygen atom-containing alkylene group, a partial chloroalkylene group or a partial chloro(ether type oxygen atom-containing alkylene) group, and a group having at least one hydrogen atom substituted with a fluorine atom, or a group having at least one carbon-carbon single bond substituted with a carbon-carbon double bond or a carbon-carbon triple bond (hereinafter, these groups are referred generally to "($R^{H2}$) group"). In this case, the remaining two groups may be connected with each other to form a ($R^{H2}$) group, or each of the remaining two groups may be independently a group ($R^{H1}$) hydrogen atom or fluorine atom. Also, in order to obtain Compound ($1A^F$) having a perfluorocyclohexyl group or a perfluorocyclohexylene group present in $R^{bf}$, $R^{cf}$, $R^{df}$ and $R^{ef}$, it is possible to employ Compound (4) having a phenyl group or a phenylene group at the part corresponding to $R^{bH}$, $R^{cH}$, $R^{dH}$ and $R^{eH}$.

Further, Compound ($3^H$) is preferably Compound ($3^F$) wherein $R^{a1}$ is $R^{af}$ and $X^1$ is a fluorine atom. Compound (5) is preferably the following Compound ($5^F$). Compound (3) which is a product of pyrolysis reaction may be employed as said compound ($3^F$).

  Formula $3^F$

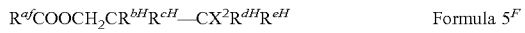  Formula $5^F$

The reaction between Compound ($3^H$) and Compound (4) can be carried out under conditions of usual esterification reaction. Compound (5) formed by the esterification reaction forms Compound ($1A^F$) by liquid-phase fluorination. The esterification reaction is carried out preferably by employing Compound ($3^F$) in an amount of an equivalent time mol amount or higher than an amount of Compound (4). In this case, Compound ($3^F$) works also as a solvent for the esterification reaction, and the product of the esterification reaction becomes a mixture of Compound ($5^F$) and Compound ($3^F$). Further, it is preferable to carry out the following described liquid-phase fluorination reaction by employing said mixture as it is. In this case, it is particularly preferable since work-up process can be omitted and Compound ($3^F$) works as a liquid phase for the liquid-phase fluorination reaction.

The liquid-phase fluorination reaction of Compound (5) is preferably carried out by reacting Compound (5) with fluorine ($F_2$) in liquid phase. The liquid-phase fluorination reaction is preferable since it can produce Compound ($1A^F$) at a satisfactory yield and the reaction can be easily controlled.

With regard to an amount of fluorine used in the fluorination reaction, it is preferable to charge a fluorine gas in such an amount as to constantly provide an excess equivalent amount of fluorine (i.e. exceeding 1 time mol amount) to a hydrogen atom in Compound (5). When continuously introducing the fluorine gas, it is particularly preferable to use fluorine in such an amount as to constantly provide at least 1.5 time equivalent amount (i.e. at least 1.5 time mols) to a hydrogen atom in Compound (5) in respect to selectivity. Also, when introducing Compound (5) into the reaction system, it is preferable to continuously introduce it. In this case, Compound (5) may be diluted at the time of introducing or Compound (5) may be introduced as it is. When continuously introducing Compound (5), it is preferable to provide fluorine constantly in an excess amount to a hydrogen atom in Compound (5).

In the method for reacting fluorine in a liquid phase, it is preferable to employ a method of continuously introducing Compound (5) into the liquid phase. Fluorine may be previously present in the liquid phase, or a fluorine gas may be continuously introduced into the reaction system, but the latter process is preferable in respect that an amount of Compound (5) can be adjusted to the fluorine gas. Further, it is particularly preferable to have fluorine previously present in the liquid phase and to continuously introduce a fluorine gas into the system during reaction.

It is preferable to use a solvent not containing a C—H bond but containing a C=F bond as an essential feature for a liquid phase, and preferable examples of the solvent include perfluoroalkanes or an organic solvent prepared by perfluorinating a well-known organic solvent having at least one kind of atom selected from a chlorine atom, a nitrogen atom and an oxygen atom in its structure. Further, as the solvent, it is preferable to employ a solvent satisfactorily dissolving Compound (5), particularly a solvent capable of dissolving at least 1 mass % of Compound (5), more particularly a solvent capable of dissolving at least 5 mass % of Compound (5).

It is preferable that a solvent used as the liquid phase dissolves a fluorine gas and is selected from solvents inert to the fluorine gas, and their preferable examples include perfluoroalkanes (tradename: FC-72 and the like), perfluoroethers (tradename: FC-75, FC-77 and the like), perfluoropolyethers (tradename: KRYTOX, FOMBLIN, GALDEN, DEMNUM and the like), chlorofluorocarbons (tradename: FLON LUBE), chlorofluoropolyethers, perfluoroalkylamines (such as perfluorotrialkylamine), inert fluids (tradename: FLUORINERT), perhalogenoester compounds (such as Compound ($1A^F$)), and perfluoroether or chorofluoropolyether solvents having a —COF group at the terminal (such as compound ($3^F$)). Also, when the above Compound (3) or Compound ($1A^F$) is selected as a solvent, it is preferable since the above-mentioned conditions are satisfied and separation of a product after the fluorination reaction is not necessary. Further, it is particularly preferable to employ Compound ($3^F$) used in an excess amount in the esterification reaction as the liquid phase.

An amount of a solvent used as a liquid phase is preferably at least 5 times mass amount, more preferably 10 to 100 times mass amount to Compound (5).

When reacting Compound (5) with fluorine in a liquid phase, it is preferable that Compound (5) is a compound having a fluorine content satisfactorily soluble in the liquid phase and that the structure of Compound (5) is adjusted so as to make a compound having a molecular weight sufficient to control the liquid phase reaction. Thus, a solvent which easily dissolves the fluorine gas is usually used as a liquid phase. In order to make Compound (5) easily soluble in the solvent, it is preferable that Compound (5) is a fluorine-containing compound, particularly Compound ($5^F$). A fluorine content of Compound (5) is preferably at least 10 mass %, more preferably from 10 to 86 mass %, most preferably from 30 to 76 mass %. Also, when Compound (5) has a sufficient molecular weight, it evaporates in a gas phase to prevent decomposition reaction during fluorination reaction, and it is therefore preferable that Compound (5) has a molecular weight of from 200 to 1000. As said Compound (5), it is preferable that $R^{a1}$ in Compound (5) is the same group as $R^{af}$.

At the time of fluorination reaction, an alkali metal fluoride (preferably NaF or KF) may be present in the reaction system as a scavenger of HF. Further, at the latter stage of fluorination reaction, it is possible to raise a yield of a fluorination reaction product by adding a compound generating a fluorine radical or by irradiating ultraviolet rays into the reaction system. Examples of the compound which can generate a fluorine radical include aromatic compounds such as benzene and toluene.

A particularly preferable production method of the present invention is a method comprises carrying out esterification reaction of at least 1 time mol of Compound ($3^F$) to Compound (4) to obtain a mixture of Compound ($5^F$) and Compound ($3^F$), subjecting the mixture to liquid-phase fluorination reaction to obtain a mixture of Compound ($1A^F$) and Compound ($3^F$), and pyrolyzing the mixture.

Further, in said method, when $R^{af}$ is —$CR^{bf}R_{cf}$—$CXR_{df}R^{ef}$, a step of separating a product of pyrolysis reaction can be omitted or simplified, such being particularly preferable. In the above preferable method, when Compound ($3^F$) is used as a solvent for the esterification reaction and works as a liquid phase for the fluorination reaction, it becomes the aimed unsaturated Compound (2) by pyrolysis reaction, such being particularly preferable.

According to the production method of the present invention, Compound (2) of desired structure can be produced at a satisfactory yield by one step reaction. The yield of the pyrolysis reaction is preferably at least 50%, more preferably at least 75%. Also, when a reaction temperature of the pyrolysis reaction is low, FCO—$CR^bR_cCXR^dR^e$(3B) may be by-produced, but it is preferable to fix the reaction conditions so as to suppress the yield of said Compound (3B) to at most 10%.

Since the Compound (2) thus obtained contains a polymerizable unsaturated group, said Compound (2) may be polymerized or may be copolymerized with a monomer polymerizable with said Compound (2) to obtain a useful polymer.

The monomer polymerizable with said Compound (2) is not specially limited, and may be selected from known polymerizable monomers. A well-known reaction procedure may be employed as a procedure for the polymerization reaction as it is. For example, when Compound (2) is perfluoro(alkyl vinyl ether), examples of a monomer polymerizable therewith include fluoroethylenes such as $CF_2$=$CF_2$, $CF_2$=$CFCl$ or $CF_2$=$CH_2$, fluoropropylenes such as $CF_2$=$CFCF_3$, (perfluoroalkyl)ethylenes having a $C_4$-$C_{12}$ perfluoroalkyl group such as $CF_3CF_2CF_2CF_2CH$=$CH_2$ or $CF_3CF_2CF_2CF$=$CH_2$, vinyl ethers having a group convertible into a carboxylic acid group or a sulfonic acid group such as $CH_3OC$(=O)$CF_2CF_2CF_2OCF$=$CF_2$ or $FSO_2CF_2CF_2OCF(CF_3)CF_2OCF$=$CF_2$, and olefins such as ethylene, propylene or isobutylene.

A polymer obtained in the present invention becomes a useful resin. Also, when Compound (2) is a fluorine-containing compound, a fluorine-containing polymer obtained by polymerizing this compound is useful as a fluororesin. The fluororesin has excellent heat resistance and chemical resistance, and is widely used in various fields.

In the present invention, a reaction mechanism of pyrolysis reaction of Compound (I) is not necessarily clear, but the following two reaction mechanisms are considered.

(Reaction mechanism 1) Compound (I) is decomposed to form $FCOCR^bR^c$—$CXR^dR^e$, from which FCOX is eliminated to form Compound (2).

(Reaction mechanism 2) Compound (I) is decomposed to form $FCOCR^bR^c$—$CXR^dR^e$, the —COF group of which is reacted with an alkali metal salt, an alkali earth metal salt or a glass surface and is converted into —COOM (M is an alkali metal atom, an alkali earth metal atom or Si≡), and from which carbon dioxide and MX are eliminated to form Compound (2).

The pyrolysis reaction is a reaction which is caused by a structure of —$COOCF_2C$—CX— present in Compound (I), and various Compounds (2) are easily produced by this reaction.

Hereinafter, the present invention is described in more details, but should not be limited thereto. In the following description, "litter" is expressed by L, "stainless steel" is expressed by SUS, "gas chromatography" is expressed by GC, "high resolution mass spectrum" is expressed by HR-MS, "gas chromatography mass analyzer" is expressed by GC-MS, "1,1,2-trichloro-1,2,2-trifluoroethane" is expressed by R-113, and "pressure" is expressed by gauge pressure.

EXAMPLE 1

Preparation Example of $CF_3CF_2CF_2OCF$=$CF_2$ (No.1)

A GC thermostat was equipped with a SUS-made column having an internal diameter of 3 mm and a length of 6 m and a SUS-made column of an internal diameter of 3 mm and a length of 3 m having $Na_2CO_3$ (7 g) of an average particle size of 160 μm filled therein, placed in series, and the thermostat was adjusted to 250° C. and a GC injection was adjusted at 150° C. A He gas was passed through GC in an amount of 50 mL/min, and a GC outlet was equipped with a dry ice/ethanol trap.

$CF_3CF_2CF_2OCF(CF_3)COOCF_2CF(CF_3)OCF_2CF_2CF_3$ (purity 99%, 50 μL) prepared by the following Example 4 was poured by injection. $CF_3CF_2CF_2OCF(CF_3)COF$ was not detected and it was confirmed that $CF_3CF_2CF_2OCF=CF_2$ was quantitatively formed. A peak of $^{19}F$-NMR (564.6 MHz, solvent $CDCl_3$, standard: $CFCl_3$) of the product corresponded to that of a standard sample.

EXAMPLE 2

Preparation Example of $CF_3CF_2CF_2OCF=CF_2$ (No. 2)

A salt bath (alkali metal nitrate) was equipped with a SUS-made column having an internal diameter of 20 mm and a length of 1 m and a SUS-made fluidized bed reactor of an internal diameter of 45 mm and a height of 400 mm having 280 g of $Na_2CO_3$ of an average particle size of 160 μm filled therein, placed in series, and a temperature in the salt bath was adjusted at 270° C. A nitrogen gas was passed through the reactor at a rate of 1520 mL/min, and $CF_3CF_2CF_2OCF(CF_3)COOCF_2CF(CF_3)OCF_2CF_2CF_3$ (purity: 99%) prepared in the following Example 4 was fed thereto by a quantitative pump at a rate of 60.2 g/hour for 1.8 hours. The reaction outlet was equipped with a dry ice/ethanol trap to recover a product. $CF_3CF_2CF_2OCF(CF_3)COF$ was not detected, and $CF_3CF_2CF_2OCF=CF_2$ was formed at a yield of 80%. A peak of $^{19}F$-NMR (564.6 MHz, solvent $CDCl_3$, standard: $CFCl_3$) of the product corresponded to that of a sample product.

EXAMPLE 3

Preparation Example of Polymer

The compound obtained in the method of Example 2 was subjected to polymerization reaction in the same manner as in the method disclosed in JP-A-6-340719. That is, a stainless steel-made reactor having an internal volume of 1.2 L was evacuated, and water (470 g), $CF_2ClCF_2CHClF$ (292 g), methanol (19 g), $CF_3CF_2CF_2OCF=CF_2$ (35 g) obtained by the method of Example 2 and $CF_2=CF_2$ (80 g) were charged therein. A temperature was maintained at 50° C., and 1 wt % perfluorohexane solution of di(perfluorobutyryl) peroxide as a polymerization initiator was charged therein to initiate the reaction.

During the reaction, $CF_2=CF_2$ was introduced into the system, and a reaction pressure was maintained at 13.5 $kg/cm^2$. The polymerization initiator was intermittently charged so as to make a polymerization rate substantially constant, and 7 cc was charged in total. After 3.2 hours, 125 g of a white copolymer was obtained in a slurry state. This copolymer had a melting point of 307° C. and a pyrolysis initiation point of 480° C., and a satisfactory compressed molded product was obtained at a molding temperature of 340° C. The molded product had a tensile strength of 392 $kg/cm^2$ and a tensile elongation of 367%.

EXAMPLE 4

Preparation Example of $CF_3CF_2CF_2OCF(CF_3)$ $COOCF_2CF(CF_3)OCF_2CF_2CF_3$ (No. 1)

EXAMPLE 4-1

Preparation Example of $CF_3CF_2CF_2OCF(CF_3)$ $COOCH_2CH(OCH_2CH_2CH_3)CH_3$ $CH_3CH_2CH_2O(CH_3)CHCH_2OH$ (16.5 g) was placed in a flask, and was stirred by bubbling a nitrogen gas therein. $CF_3CF_2CF_2OCF(CF_3)COF$ (46.5 g) was dropwise added for 2 hours while maintaining an internal temperature at 26 to 31° C. After finishing the dropwise adding, the reaction content was stirred at room temperature for 2 hours, and a saturated sodium hydrogencarbonate aqueous solution (50 mL) was added at an internal temperature of at most 15° C. Water (50 mL) and chloroform (135 mL) were added thereto, and the mixture was separated to obtain a chloroform layer as an organic layer. The organic layer thus obtained was washed with water (50 mL), and was dried by magnesium sulfate, and was filtrated to obtain a crude liquid.

The crude liquid thus obtained was concentrated by an evaporator, and was then distilled under a reduced pressure to obtain fraction (1) (29 g) at 23 to 52° C./4.0 kPa, fraction (2) (19 g) at 52 to 61° C./3.6 to 4.0 kPa and fraction (3) (4 g) at 52 to 70° C./1.3 to 3.6 kPa. A GC purity was 68% in case of fraction (1), 98% in case of fraction (2) and 97% in case of fraction (3). NMR spectrum of fraction (2) was measured, and it was confirmed that the main component was $CF_3CF(OCF_2CF_2CF_3)COOCH_2CH(OCH_2CH_2CH_3)$ $CH_3$ and a mixture of diastereomers.

NMR Spectrum of Fraction (2)

$^1H$-NMR(399.8 MHz, solvent $CDCl_3$, standard:TMS) δ (ppm):0.90 (t, J=7.5 Hz, 3H), 1.20(d, J=5.4 Hz, 3H), 1.50–1.60(m, 2H), 3.33–3.50(m, 2H), 3.64–3.74(m, 1H), 4.23–4.29(m, 1H), 4.34–4.41(m, 1H).

$^{19}F$-NMR(376.2 MHz, solvent $CDCl_3$, standard:$CFCl_3$) δ (ppm): −80.9(1F), −82.3(3F), −83.1(3F), −87.4(1F), −130.7 (2F), −132.7 (1F).

Also, it was confirmed by GC that the main component contained in fraction (1) and fraction (3) was $CF_3CF_2CF_2OCF(CF_3)COOCH_2CH(OCH_2CH_2CH_3)CH_3$.

EXAMPLE 4-2

Preparation Example of $CF_3CF_2CF_2OCF(CF_3)$ $COOCF_2CF(CF_3)OCF_2CF_2CF_3$ by Fluorination Reaction Fraction (2) and fraction (3) obtained in Example 4-1 were mixed, and 19.5 g of the mixture was dissolved in R-113 (250 g) to obtain a fraction solution. On the other hand, into a nickel-made autoclave of 500 mL, were added NaF (26.1 g) and R-113 (324 g), and the mixture was stirred and was cooled to −10° C. After blowing a nitrogen gas therein for 1 hour, a fluorine gas diluted to 20% by a nitrogen gas was blown therein at a rate of 5.66 L/h for 1 hour, and while maintaining the blowing at the same rate, the above obtained fraction solution was poured therein for 19.4 hours.

Thereafter, while maintaining the blowing of the fluorine gas diluted to 20% by a nitrogen gas at the above-mentioned rate, a R-113 solution (0.01 g/mL) of benzene was poured therein, and an outlet valve of the autoclave was closed, and an inlet valve of the autoclave was closed when the pressure reached 0.12 MPa, and stirring was continued for 1 hour.

Further, the above procedure was repeated 4 times while raising a temperature from −10° C. to room temperature, and thereafter the above procedure was repeated 5 times at room temperature. During this procedure, benzene was charged in an amount of 0.291 g in total and R-113 was charged in an amount of 45.0 g in total. Thereafter, a nitrogen gas was blown therein for 2 hours, and the reaction mixture was recovered by decantation. The crude liquid thus obtained was concentrated by an evaporator, and the product was quantitatively determined by $^{19}F$-NMR, and its yield was 69%. A part of the crude liquid was distilled under a reduced pressure, and was purified to obtain $CF_3CF_2CF_2OCF(CF_3)$ $COOCF_2CF(CF_3)OCF_2CF_2CF_3$. The product thus obtained was a mixture of diastereomers.

Boiling point: 46~51° C./5.2 kPa.

HR-MS (CI method) 664.9496(M+H. Theoretical value:$C_{12}HF_{24}O_4$=664.9492).

$^{19}$F-NMR (564.6 MHz, solvent $CDCl_3/C_6F_6$, standard: $CFCl_3$) δ (ppm): −80.6(1F), −80.8 and −80.9(3F), −81.6~−83.1(2F), −82.6 (6F), −82.8(3F), −86.7(1F), −87.4(1F), −87.5(1F), −130.6(4F −132.2(1F), −145.7 and −145.9(1F).

$^{13}$C-NMR(150.8 MHz, solvent $CDCl_3/C_6F_6$, standard:$CDCl_3$) δ (ppm):100.26 and 100.28, 102.8, 106.8, 107.0, 116.0, 116.2, 116.5 and 116.6, 117.4, 117.5, 117.9, 117.9, 152.2 and 152.3.

EXAMPLE 5

Preparation Example of $CF_3CF_2CF_2OCF(CF_3)$ $COOCF_2CF(CF_3)OCF_2CF_2CF_3$ (No. 2)

EXAMPLE 5-1

Preparation Example of $CF_3CF_2CF_2OCF(CF_3)$ $COOCH_2CH(OCH_2CH_2CH_3)CH_3$ $CH_3CH_2CH_2OCH(CH_3)CH_2OH$ (620.1 g) was placed in a flask, and was stirred by bubbling a nitrogen gas therein. $CF_3CF_2CF_2OCF(CF_3)COF$ (3604 g) was dropwise added for 8 hours while maintaining an internal temperature at 25 to 35° C. After finishing the dropwise adding, a reaction mixture containing the above aimed compound and $CF_3CF_2CF_2OCF(CF_3)COF$ was stirred for 2 hours at room temperature for continuously bubbling a nitrogen gas therein, and the reaction mixture was then used in the reaction of the following Example 5-2.

EXAMPLE 5-2

Preparation Example of $CF_3CF_2CF_2OCF(CF_3)$ $COOCF_2CF(CF_3)OCF_2CF_2CF_3$ by Fluorination Reaction $CF_3CF_2CF_2OCF(CF_3)COF$ (2340 g) was added to a nickel-made autoclave of 3000 mL, and was stirred and maintained at 25° C. A gas outlet of the autoclave was equipped with a cooler maintained at 20° C., a NaF pellet-filled layer and a cooler maintained at −10° C. placed in series. Further, the autoclave was equipped with a liquid-returning line to return a condensed liquid from the cooler maintained at −10° C. to the autoclave. After blowing a nitrogen gas therein for 1.5 hours, a fluorine gas diluted to 20 vol % by a nitrogen gas was blown therein at a rate of 8.91 L/h for 3 hours.

Thereafter, while blowing the diluted fluorine gas at the same rate, the reaction mixture (106 g) obtained in the above Example 5-1 was charged therein for 45.6 hours.

Thereafter, while blowing the diluted fluorine gas at the same rate, 18 mL of a $CF_3CF_2CF_2OCF(CF_3)COF$ solution having a benzene concentration of 0.01 g/mL was charged while raising a temperature from 25° C. to 40° C., and the benzene-charging inlet of the autoclave was closed and an outlet valve of the autoclave was also closed, and a fluorine gas inlet valve of the autoclave was closed when the pressure reached 0.20 MPa, and the content was continuously stirred for 1 hour. The pressure was then returned to normal pressure, and while maintaining the internal temperature of the reactor at 40° C., 6 mL of the above benzene solution was charged, and the benzene-charging inlet of the autoclave was closed and the outlet valve of the autoclave was then closed, and the fluorine gas inlet valve of the autoclave was also closed when the pressure reached 0.20 MPa, and the content was continuously stirred for 1 hour. Further, the same procedure was repeated one time.

The total charging amount of benzene was 0.309 g and the total charging amount of $CF_3CF_2CF_2OCF(CF_3)COF$ was 30 mL. Further, a nitrogen gas was blown therein for 2.0 hours. After the reaction, distillation-purification was carried out to obtain a mixture of the above aimed compound (85.3 g) and $CF_3CF_2CF_2OCF(CF_3)COF$ as a crude liquid. The aimed compound thus obtained had a purity of 95%.

EXAMPLE 6

Preparation Example of $CF_3CF_2CF_2OCF=CF_2$ by Gas Phase Pyrolysis (No. 3)

390 g of $Na_2CO_3$ powder was filled into a fluidized bed reactor comprising a stainless steel-made cylindrical container (internal diameter 51 mm, length 400 mm) equipped with porous plates (filtration accuracy 0.5 μm, stainless steel-made) at the upper and lower parts. $Na_2CO_3$ had a particle size in a range of from 100 to 250 μm. This reactor was placed in a molten salt bath heated at 260° C., and a nitrogen gas was flown at a rate of 234 NL/hour for 8 hours from the bottom of the reactor to dehydrate $Na_2CO_3$. Thereafter, while maintaining the reactor temperature at 260° C., $CF_3CF_2CF_2OCF(CF_3)COOCF_2CF(CF_3)OCF_2CF_2CF_3$ crude liquid having a purity of 95% obtained in Example 5 was diluted with a nitrogen gas and was continuously fed from the bottom of the reactor, and a gas flowing out of the upper part of the reactor was liquefied and recovered by a dry ice trap. The feeding rate of the crude liquid was 160 g/hour and the feeding rate of nitrogen gas was 205 L/hour.

Three hours after the initiation of reaction, a reactor outlet gas was analyzed by GC, and as this results, a conversion of $CF_3CF_2CF_2OCF(CF_3)COOCF_2CF(CF_3)OCF_2CF_2CF_3$ was 96.7% and a selectivity of $CF_3CF_2CF_2OCF=CF_2$ was 95.4%. Also, a selectivity of $CF_3CF_2CF_2OCF(CF_3)COF$ was 1.8%.

EXAMPLE 7

Preparation Example of $Cy^FCF_2OCF=CF_2$ $Cy^FCF_2OCF(CF_3)COOCF_2CF(CF_3)OCF_2CF_2CF_3$ was charged by injection in place of $CF_3CF_2CF_2OCF(CF_3)$ $COOCF_2CF(CF_3)OCF_2CF_2CF_3$ in the same manner as in Example 1. Its product was analyzed by HR-MS, and it was confirmed that the aimed compound was quantitatively formed.

EXAMPLE 8

Preparation Example of $CF_3(CF_2)_9OCF=CF_2$ $CF_3(CF_2)_9OCF(CF3)COOCF_2CF\ (CF_3)OCF_2CF_2CF_3$ was charged by injection in place of $CF_3CF_2CF_2OCF(CF_3)$ $COOCF_2CF(CF_3)OCF_2CF_2CF_3$ in the same manner as in Example 1. Its product was analyzed by HR-MS, and it was confirmed that the aimed compound was quantitatively formed.

INDUSTRIAL APPLICABILITY

According to the present invention, Compound (2) which was heretofore difficult to be synthesized or Compound (2) which was heretofore synthesized by an economically unfavorable method, can be prepared from Compound (I) at a high yield in a short step. Particularly, Compound (1A) is generally easily available, easily producible and cheap, and compounds of various structures are easily available, and various unsaturated compounds can be produced by using said compounds as a starting material.

Also, by appropriately selecting structures of $R^{a1}$ and further $R^{bH}$, $R^{cH}$, $R^{dH}$ and $R^{eH}$ in the formula 1A, Compound (1A) usable as a starting material for pyrolysis reaction can be favorably prepared, which becomes easily soluble in a solvent at the time of fluorination and accelerates a liquid-phase fluorination reaction, thereby proceeding the fluorination reaction at a high yield.

Further, according to the present invention, a novel compound useful as a starting material for fluororesin can be provided.

The entire disclosure of Japanese Patent Application No. 2000-166773 filed on Jun. 2, 2000 including specification, claims and summary is incorporated herein by reference in its entirety.

What is claimed is:

1. A method for preparing a compound represented by Formula ($2^F$)

$$CR^{bf}R^{cf}=CR^{df}R^{ef} \quad \text{Formula } (2^F)$$

said method comprising:

pyrolyzing a compound represented by Formula ($1B^F$)

$$CXR^{df}R^{ef}\text{—}CR^{bf}R^{cf}\text{—}COOCF_2CR^{bf}R^{cf}\text{—}CXR^{df}R^{ef} \quad \text{Formula } (1B^F)$$

in a gas phase in the presence of a solid catalyst without using a solvent, wherein $R^{bf}$, $R^{cf}$, $R^{df}$, and $R^{ef}$ is independently a fluorine atom or a fluorine-containing monovalent organic group which is not capable of changing during said pyrolyzing; or two of $R^{bf}$, $R^{cf}$, $R^{df}$, and $R^{ef}$ groups are connected with each other to form a fluorine-containing divalent organic group which is not capable of changing during said pyrolyzing, and the two remaining groups are independently a fluorine atom or a fluorine-containing monovalent organic group which is not capable of changing during said pyrolyzing; and X is a halogen atom.

2. The method as claimed in claim 1, wherein said solid catalyst is a glass, an alkali metal salt, or an alkali earth metal salt.

3. The method according to claim 1, wherein said solid catalyst is a glass or an alkali metal salt.

4. The method according to claim 1, wherein said solid catalyst is a glass having a particle size of from 100 to 250 µm.

5. The method according to claim 1, wherein said solid catalyst is an alkali metal salt having a particle size of from 100 to 250 µm.

6. The method as claimed in claim 1, wherein said pyrolyzing is carried out at a temperature of from 200° C. to 500° C.

7. The method as claimed in claim 1, wherein said pyrolyzing is carried out at a temperature of from 250° C. to 450° C.

8. The method according to claim 1, wherein said pyrolyzing is carried out by continuously supplying the compound represented by Formula ($1B^F$) from a lower part of a fluidized bed reactor.

9. The method according to claim 1, wherein the yield of said compound represented by Formula ($2^F$) is at least 50%.

10. The method according to claim 1, wherein the yield of said compound represented by Formula ($2^F$) is at least 75%.

11. The method as claimed in claim 1, wherein said compound represented by Formula ($1B^F$) is $CF_3CF_2CF_2OCF(CF_3)COOCF_2CF(CF_3)OCF_2CF_2CF_3$ and said compound represented by Formula ($2^F$) is $CF_3CF_2CF_2OCF=CF_2$.

12. The method according to claim 11, wherein said compound represented by $CF_3CF_2CF_2OCF(CF_3)COOCF_2CF(CF_3)OCF_2CF_2CF_3$ is a compound obtained by liquid-phase fluorination of a compound represented by $CF_3CF_2CF_2OCF(CF_3)COOCH_2CH(CH_3)OCH2CH_2CH_3$ obtained by reacting a compound represented by $CF_3CF_2CF_2OCF(CF_3)COF$ and a compound represented by $HOCH_2CH(CH_3)OCH_2CH_2CH_3$.

13. A method for preparing a polymer, said method comprising:

polymerizing a compound represented by Formula ($2^F$) prepared by the method as claimed in claim 1 or polymerizing a polymerizable monomer with said compound represented by Formula ($2^F$) wherein said polymerizable monomer is capable of being polymerized with said compound represented by Formula ($2^F$).

14. The method according to claim 13, wherein said compound represented by Formula ($2^F$) is $CF_3CF_2CF_2OCF=CF_2$.

* * * * *